United States Patent [19]
Hoffmann et al.

[11] Patent Number: 5,703,342
[45] Date of Patent: Dec. 30, 1997

[54] TEMPERATURE CONTROL METHOD USING EMPIRICALLY DETERMINED CHARACTERISTICS

[75] Inventors: Erwin Hoffmann, Hohen Neuendorf; Christian Lüdke; Jochen Skole, both of Berlin, all of Germany

[73] Assignee: Bodenseewerk Perkin-Elmer GmbH, Überlingen, Germany

[21] Appl. No.: 734,162

[22] Filed: Oct. 21, 1996

Related U.S. Application Data

[63] Continuation of Ser. No. 257,690, Jun. 9, 1994, abandoned.

[30] Foreign Application Priority Data

Jun. 14, 1993 [DE] Germany ............... 43 19 652.7

[51] Int. Cl.$^6$ ................................. H05B 1/02
[52] U.S. Cl. ................... 219/497; 219/492; 374/1; 374/103; 364/166
[58] Field of Search ................. 219/492, 497, 219/506, 501, 490, 491, 494; 99/331, 332, 339, 337, 329 R; 364/149–153, 106; 374/1, 102, 103

[56] References Cited

U.S. PATENT DOCUMENTS

| | | | |
|---|---|---|---|
| 3,346,341 | 10/1967 | Sternberg . | |
| 4,194,826 | 3/1980 | Lewis | 354/299 |
| 4,913,038 | 4/1990 | Burkett et al. | 99/331 |
| 5,026,971 | 6/1991 | Payne et al. | 219/483 |
| 5,422,806 | 6/1995 | Chen et al. | 364/142 |
| 5,427,720 | 6/1995 | Kotzab | 264/40.6 |

FOREIGN PATENT DOCUMENTS

| | | |
|---|---|---|
| 7603377 | 9/1976 | France . |
| 2657309 | 6/1977 | Germany . |
| 3108470 | 9/1982 | Germany . |
| 2008235 | 6/1983 | Germany . |
| 3333724 | 4/1985 | Germany . |
| 3334875 | 4/1985 | Germany . |
| 3153413 | 6/1988 | Germany . |
| 3718809 | 12/1988 | Germany . |
| 3202825 | 7/1992 | Germany . |
| 4117436 | 12/1992 | Germany . |
| 4223133 | 1/1993 | Germany . |
| 1166076 | 7/1985 | U.S.S.R. . |
| 1564648 | 4/1980 | United Kingdom . |
| 2238887 | 6/1991 | United Kingdom . |

OTHER PUBLICATIONS

Sandweg–Kohmann, Astrid: Regelung eines ereignisdiskreten Stuckprozesses. In: at.—Automatisierungstechnik, 40, 1992, S. 357–361, Kap. 2,3,5.

Montaser, Akbar; Crouch, S.R.; New Methods for Programmed Heating of Electrically Heated Nonflame Atomic Vapor Cells. In: Analytical Chemistry, vol. 47, No. 1, Jan. 1975, S.38–45.

*Primary Examiner*—Mark H. Paschall
*Attorney, Agent, or Firm*—David Aker; Edwin T. Grimes

[57] ABSTRACT

The present invention relates to a method for controlling the temperature of a system in accordance with a desired temperature curve which is divided into predetermined time intervals. It is the object of the present invention to control the temperature of the system in such a manner that the predetermined and desired temperature curve is observed as exactly as possible. The temperature control method is characterized in that the heating power to be applied to the heating device during one time interval is determined in response to the desired temperature and the heating-up rate of the respective time interval by using empirically determined dynamic heating-up and cooling characteristics typical of the system, that the heating power determined for each time interval is converted according to a calibration curve into a set value for a voltage control device, that the heating power actually applied to the heating device is determined within each time interval, said heating power having assigned thereto a set comparative value by means of the calibration curve, and that, when the set value deviates from the set comparative value by more than a predetermined and set tolerance value within the respective time interval, the set value of the respectively successive time interval is changed in response to said deviation.

22 Claims, 8 Drawing Sheets

5,703,342

TEMPERATURE CONTROL METHOD USING EMPIRICALLY DETERMINED CHARACTERISTICS

This application is a continuation of application Ser. No. 08/257,690, filed on Jun. 9, 1994, now abandoned.

TECHNICAL FIELD

The present invention relates to a method for controlling the temperature of a system in accordance with a desired temperature curve which is divided into predetermined time intervals and has a desired temperature assigned to each time interval, with the system being heated up by heating power applied to a heating device.

BACKGROUND ART

Such temperature control methods are, for instance, required in atomic absorption or atomic emission spectroscopy in which heating up to temperature values of more than 2500° C. and subsequent cooling are performed for atomizing a sample contained in a suitable and heatable electrothermal system, such as a graphite tube atomizer, in accordance with an exactly predetermined, relatively complicated temperature curve. To be able to carry out a measurement which is as exact as possible and can be repeated, the given temperature curve must strictly be observed. To achieve such a goal, the temperature curve is divided into time intervals according to prior-art methods, with the time intervals having each assigned thereto a desired temperature value. The time intervals are sufficiently long, so that the system, which has an electrical heating power supplied thereto, can reach an equilibrium state of increased temperature at the end of the time interval, i.e., a state in which the supplied heating power is substantially equal to the outgoing power dissipated, e.g., by reason of heat conduction, radiation or convection. This, however, leads to the restriction that only temperature curves with a relatively long run and slow heating and cooling processes can be realized. Especially temperature curves having great temperature rising rates do not yield satisfactory results in such an atomic absorption or atomic emission spectrometer.

With short time intervals, the system can no longer reach its equilibrium state because of the response delay times on account of the finite speed of heat transmission during the heating process or cooling process. Nevertheless, in order to achieve the desired rise in temperature within a short time interval, the heating powers by means of which the desired temperature value is maintained in the equilibrium state is multiplied by an empirically determined correction function. A desired temperature curve in the case of which great changes in the heating-up rate arise within neighboring time intervals cannot be implemented in a precise manner. For instance, excessive temperatures arise in this method during transition from a time interval with a very high heating-up rate to a time interval with a constant temperature. Moreover, since the correction function is empirically determined on a system under predetermined conditions, a deviation of the actually obtained temperature curve from the desired temperature curve may be observed when the system does not meet these predetermined conditions.

SUMMARY OF THE INVENTION

It is therefore an object of the present invention to provide a method which is used for controlling the temperature of a system and precisely achieves a desired temperature curve divided into predetermined time intervals.

This object is achieved according to the invention with a temperature control method of the above-mentioned kind which is characterized in that the heating power to be applied to the heating device during one time interval is determined in response to the desired temperature and the temperature curve steepness of the respective time interval by using empirically determined dynamic heating-up and cooling characteristics typical of the system, that the heating power determined for each time interval is converted according to a calibration curve into a set value for a heating power control, that the heating power actually applied to the heating device is determined in each time interval, with the heating power having assigned thereto a set comparative value by means of the calibration curve, and that, when the set value deviates from the set comparative value by more than a predetermined tolerance value within the respective time interval, the set value of the respectively following time interval is changed in response to said deviation.

A precise and desired temperature curve can also be achieved at high heating-up rates and very short time intervals with such a method.

Since not only the desired temperature is considered but also the temperature curve steepness for the respective time interval so as to determine the heating power values converted by means of a calibration curve into a set value and since empirically determined heating and cooling characteristics of the system are used, the heat transmission behavior from the heating device to the system is thereby considered empirically, so that an exact real temperature curve following the desired temperature curve can be achieved. In particular, an excessive increase in temperature upon change in the heating-up rate or temperature curve steepness from high to low values is prevented.

The heating power to be applied to the heating device is determined in response to the desired temperature and the temperature curve steepness within every time interval by using empirically determined dynamic heating and cooling characteristics of the system under specific conditions. In case the system or the heating device does not meet the specific conditions underlying the determination of the heating power, a comparison with the determined heating power becomes possible by determining the heating power actually applied to the heating device. When the deviation of the actually applied heating power from the determined heating power exceeds a predetermined tolerance value, with both powers being converted by means of a calibration curve into a set value, the set value for the heating power is changed in response to said deviation. For instance, variations in the mains voltage or changes in the electric resistance of the heating means due to temperature variations in the heating characteristics can thus be considered, whereby the desired temperature curve can be followed more exactly.

When the set value deviates from the set comparative value by more than a predetermined tolerance value within one time interval, the set value of the next time value is readjusted by addition of the difference value from the set value and the set reference value in an advantageous development of the invention. Such a readjustment has turned out to be especially advantageous in the performance of the method of the invention for achieving a predetermined and desired temperature curve in a manner which is as exact as possible. The difference value used for readjustment could additionally be provided with a multiplicative constant in an optional way.

In another advantageous development of the invention, the heating power is calculated with the aid of values which depend on the desired temperature and the heating-up rate and regard a dynamic heat capacity and a dissipated power of the system, with an equation being used in accordance with the energy conversation law. Hence, the heating power which is expressed as energy divided by the length of the time interval and supplied to the system during this time interval follows from a dynamic heat capacity which depends on the desired temperature and the temperature curve steepness of said time interval and which is multiplied by the temperature change divided by the length of the time interval, i.e., the temperature curve steepness comparable with the heating-up rate. In addition, the outgoing dissipated power of the system which depends on the desired temperature and the temperature curve steepness of the respective time interval is considered.

To determine these values that depend on the temperature and the heating-up rate and regard the dynamic heat capacity and the dissipated power, the temperature of the system is measured for the system at a predetermined heating power over the whole period until the system has reached an equilibrium state in which the dissipated power is equal to the supplied heating power, with a temperature curve typical of the system being obtained with the heating power as parameter. When the heating power is switched off at a specific temperature in the course of this temperature curve, the values which are valid for this specific temperature and for the heating-up rate existing directly before switching off can be determined for the dynamic heat capacity and the dissipated power from the determined temperature curve steepnesses immediately before and immediately after the switching off of the heating power. A field of values is determined for the dynamic heat capacity and the dissipated power for a multitude of temperature values and values of the heating-up rate. The real temperature curve can thereby be approximated to the desired temperature curve in a very precise manner because the system has been measured under many temperature and heating-up rate conditions, and the heating power to be applied is respectively determined in each time interval by using the system values measured. The accuracy at which a desired temperature curve can be approached is therefore defined, inter alia, by the number of the empirically determined values of the dynamic heat capacity and the dissipated power.

In an advantageous embodiment of the invention the heating power to be applied within a time interval is determined on the basis of the desired temperature and the temperature curve steepness within the respective time interval from a temperature-time characteristic determined empirically by using different heating powers. On the basis of the temperature-time characteristic with the heating power as the parameter, a multitude of values are determined for the heating power at different temperatures and temperature curve steepnesses with the aid of which that heating power is determined that leads to the desired temperature curve steepness at a given desired temperature within a specific time interval. When no exactly appropriate values for the heating power can be determined from the characteristic for the values of the desired temperature and the temperature curve steepness, which values are valid within the specific time interval, the heating power to be applied to the heating device is calculated by interpolation.

By analogy, a linear interpolation is performed for the dynamic heat capacity and the dissipated power when within a time interval the desired temperature and the temperature steepness deviate from the values stored in the table of values it has been found in practice that a relatively small number of values is sufficient for the dynamic heat capacity and the dissipated power in order to calculate the heating power to be applied by means of such an interpolation, with the heating power exactly meeting the desired temperature curve.

In another advantageous development of the invention the dynamic heat capacity and the dissipated power are determined at a multitude of values for the heating power in an equilibrium state of the system in which the dissipated power is equal to the heating power, and at a heating power maximally supplied to the system at a multitude of temperature values of the non-equilibrium system. This has the advantage that an exact specification of the heating and cooling characteristics of a specific system is possible with a relatively small number of measurement curves, special consideration being given to the equilibrium states of the system in which no essential temperature rise takes place, and to the states in which heating takes place at a maximum heating power and a maximum heating-up rate. The values which are actually to be achieved for the desired temperature and the heating-up rate can again be determined by linear interpolation from the values of the dynamic heat capacity and the dissipated power obtained according to this embodiment. In this preferred development the number of measurement data needed is minimum, so that the process of determining the data of the system, which has to be carried out once, requires little time.

In another advantageous development of the invention the heating-up rate is adjusted by a phase angle control. The set values for implementing the heating-up rate correspond to an operating angle of the phase angle control.

In another advantageous development of the invention, an instantaneous temperature of the system is additionally measured within each time interval for determining the heating power actually employed by the system, with the instantaneous temperature being compared with the desired temperature and, when a deviation of the instantaneous temperature from the desired temperature exceeds a predetermined value, the desired temperature of the respectively following time interval is changed in response to the deviation. Hence, the temperature of the system can additionally be monitored and readjusted, which has been found to be especially advantageous when an unexpected change in the heating and cooling characteristics of the system takes place that might lead to an unforeseen change in temperature.

Other advantageous embodiments will become apparent from the subclaims.

BRIEF DESCRIPTION OF THE DRAWINGS

The invention shall now be illustrated in more detail with reference to embodiments taken in conjunction with the drawings, in which.

DESCRIPTION OF THE PREFERRED EMBODIMENTS

Figure 1:
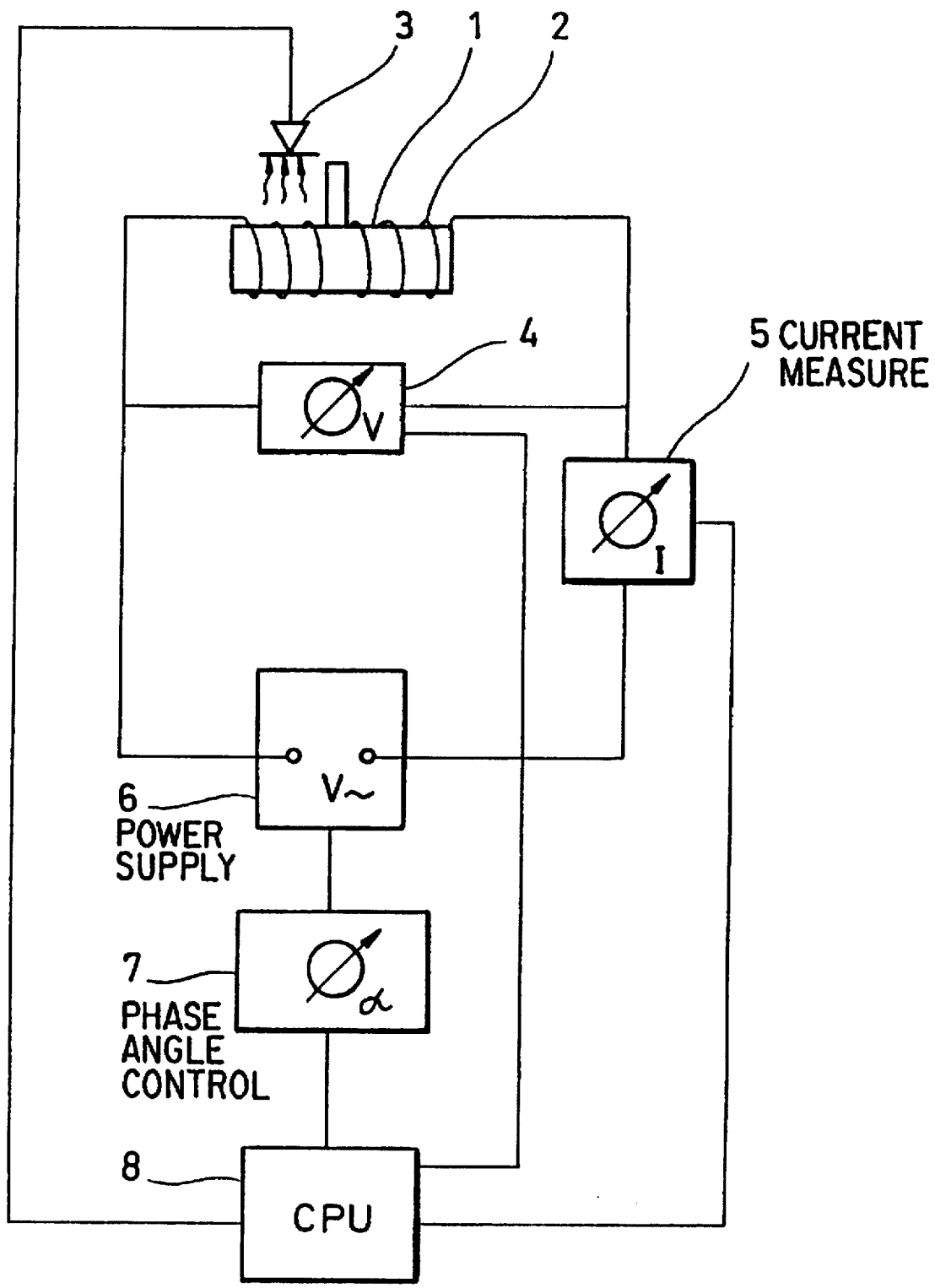
FIG. 1 is a simplified diagrammatic view of an electrothermal system for performing the method of the invention.

A simplified example of an assembly for performing the method of the invention is diagrammatically shown in FIG. 1. An elongated atomizer tube 1 which consists, e.g., of graphite and contains a sample to be atomized is coupled with a heating device 2 which comprises, for instance, a heating wire wound around the atomizer tube 1. A radiation-sensitive photodiode 3 is mounted near the atomizer tube 1. A voltage measuring device 4 is electrically connected to an input side and an output side of the heating device 2. A controllable power supply means 6 for the supply of an alternating voltage is also connected to the input and output sides of the heating device 2. A current measuring device 5 is connected between a connection of the power supply means 6 and a connection of the heating device 2. The power supply means 6 is connected to a device 7 for phase angle control and for the adjustment of an operating angle. The device 7 for the adjustment of the operating angle is connected to a computer 8 with a central processing unit. Computer 8 is also connected to outputs of photodiode 3, voltage measuring device 4 and current measuring device 5, each with A/D converters.

Apart from the simplified representation of the whole electrothermal system, as is shown in FIG. 1, for achieving a predetermined temperature characteristic on an atomizer tube, many modifications of the electrothermal system are possible. For instance, heating device 2 could also include electrodes at the end portions of the longitudinal extension of the atomizer tube, thereby permitting current flow in the longitudinal direction of the atomizer tube. Such electrodes, however, could also be arranged in end, portions positioned in a direction transverse to the longitudinal extension of the atomizer tube for permitting current flow in a direction transverse to the longitudinal extension of the atomizer tube. In such a case the atomizer tube is made from a suitable electrothermal material, such as graphite. Instead of a tube, another shape could also be chosen for the atomizer means, e.g., the shape of a pot or cup. Instead of photodiode 3 which is here used and responsive to heat rays, a pyrometer or another suitable temperature measuring device could be used. The arrangement and connection of the voltage and resistance measuring device is also just one example of a possible configuration of an electrothermal system in which the method of the invention is employed. Instead of a means for adjusting an operating angle, a device could be used for amplitude control or for pulse duration or pulse width modulation. Apart from a power supply means which supplies an alternating voltage, a power supply means with a d.c. voltage is also possible. Moreover, the atomizer tube could be coupled with a cooling means which includes, e.g., an electrothermal cooler or a coolant circuit.

Figure 2:
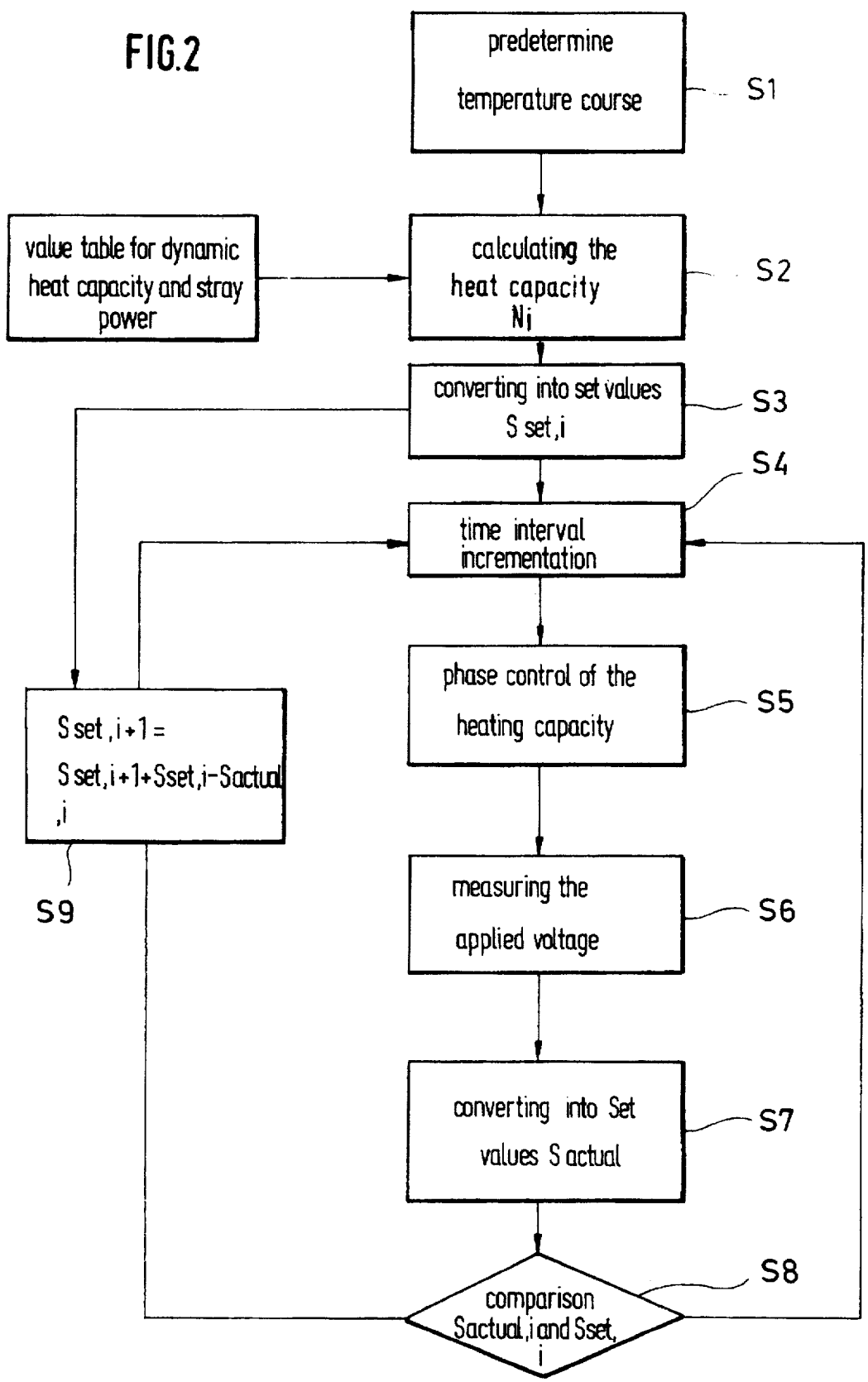
FIG. 2 is a block diagram for illustrating an embodiment of the method of the invention.

FIG. 2 is a flow diagram of an embodiment of the temperature control method of the invention which can be employed in the electrothermal system illustrated in FIG. 1. At the beginning of the method for controlling the temperature of the system, which system is to follow a predetermined and desired temperature curve, the desired temperature curve which is divided into individual time intervals is fed in a step S1 into the computer. A desired temperature value is assigned to each time interval by specification of the desired temperature curve. A heating-up rate which is expressed by the steepness of the temperature curve is determined from the length of the time intervals and the difference of the desired temperatures between two successive time intervals.

The heating power which corresponds to the predetermined and desired temperature curve and is to be applied during each time interval is calculated in the computer in the next step S2. The calculation is based on values for a dynamic heat capacity $C_w$ and a dissipated power $N_v$, which values were determined during a measuring operation carried out once for each usable atomizer tube in response to the temperature and the steepness of the temperature curve and were each stored in a table of values. The table of values may, e.g., be stored on a magnetic data carrier or may be loaded into the computer upon replacement of the atomizer tube or the heating device in accordance with the respectively existing system. A preferred embodiment for experimentally determining the two tables of values for the dynamic heat capacity $C_w$ and dissipated power $N_g$ of a specific electrothermal system will be discussed in detail further below.

An equation which is based on power values and is analogous to an energy conservation law is employed in the calculation of the heating power $N_i$ used within a time interval $\delta t_i$:

$$N_i = C_w(T_i, T'_i) \times T'_i N_v(T_i, T'_i) \qquad (1)$$

In equation (1), $T_i$ and $T'_i$ represent the desired temperature and steepness of the temperature curve, respectively, within the i-th time interval. The values for the desired temperature $T_i$ and the steepness $T'_i$ of the temperature curve are gathered from the desired temperature curve entered or are calculated by way of the additionally known duration of a time interval $\delta t_i$, as explained above. The values which belong to these desired temperature values and temperature curve steepness values and are typical of the system and regard the dynamic heat capacity and the dissipated power are taken from the tables of values and put into the equation. The heating power to be applied within time interval $\delta t_i$ is calculated in the computer therefrom.

Since the values of the dynamic heat capacity and the dissipated power are not known for all possible temperature values and temperature curve steepness values, it may happen that there are no corresponding values for $C_w$ and $N_v$ for individual pairs of values $(T_i, T'_i)$ of the desired temperature curve to be obtained. The values for the dynamic heat capacity $C_w$ and the dissipated power $N_v$ are determined in such a case by linear interpolations.

In another preferred embodiment of the temperature control method, the heating power to be applied within a specific time interval is determined in an alternative manner. The heating powers which are required in each time interval and are necessary for achieving the temperature curve steepness predetermined within each time interval on the basis of the desired temperature are gathered from a heating-up behavior typical of the system in the form of a temperature-time characteristic obtained at different heating powers. The characteristics determined before the temperature control method proper are advantageously stored in the form of tables of values for the heating power at different temperatures and temperature curve steepnesses, again on a data carrier, so that the corresponding tables of heating power values can be loaded in case of a change of the electrothermal system, e.g., due to replacement of the atomizer tube. In comparison with the previously explained method, one only needs a table of values for the heating power. Moreover, calculation of the heating power by analogy with formula (1) can be dispensed with. An interpolating operation is again performed between the values next to the desired temperature value and the temperature curve steepness of a specific time interval for the heating power according to the table stored.

Figure 7:
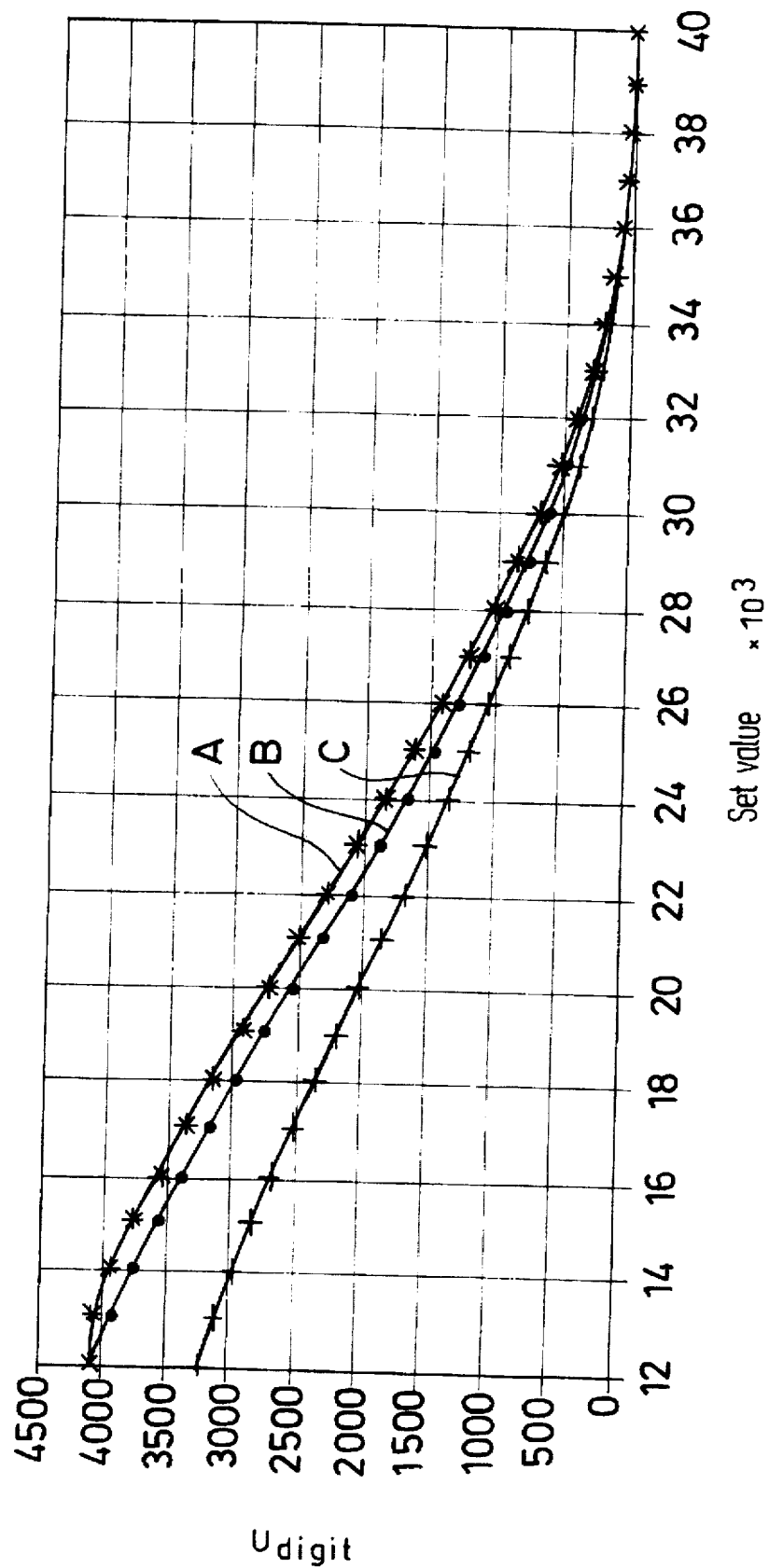
FIG. 7 shows a calibration curve for converting a set value into a value for the heating voltage.

In the next step S3, the calculated heating power $N_i$ is converted into a set value $S_{soll,i}$ for the phase angle control of the device 7 for controlling the power supply means 6. A voltage value $U_{digit,i}$ is first of all determined by taking the square root from the power value $N_i$ multiplied by the resistance of the heating device. Value $U_{digit,i}$ which corresponds to an effective value for the voltage is converted through a calibration curve, which is shown in FIG. 7, into a time count value which corresponds to the set value. The time count value which is expressed in count units of the computer specifies the operating angle of the phase angle control which controls the power supply means 6 via device 7. As becomes apparent from FIG. 7, a time count value of 40,000 corresponds to an operating angle of 180 degrees. Hence, during phase angle control the voltage value of the a.c. voltage is set to zero during the whole half-wave. Since each half-wave of the a.c. voltage is manipulated in accordance with the size of the operating angle, the effective power or $U_{digit,i}$ is zero in the present case at a count value of 40,000 or an operating angle of 180°. A decrease in the time count value effects an increase in the effective voltage value $U_{digit}$. FIG. 7 illustrates curves A, B, and C which were determined for effective values of the mains voltage of 233 V for curve A, 220 V for curve B and 190 V for curve C. The set value $S_{soll,i}$, expressed in time count values, is determined by assigning the voltage value $U_{digit,i}$ derived from the determined heating power $N_i$ in accordance with the calibration curve according to FIG. 7.

In the subsequent step S4 in FIG. 2, the temperature control method follows a loop in which the determined set values $S_{soll,i}$ are adjusted in accordance with the given desired temperature curve in successive time intervals. The time interval counting is here incremented to progress from time interval $\delta t_{i-1}$ to time interval $\delta t_i$.

In accordance with the present embodiment the duration of a time interval is fixed and constant and respectively extends over a half-wave of the alternating current used for heating. At a frequency of 50 Hz for the a.c. supply voltage, the duration of each time interval is 10 ms. However, time intervals of respectively different durations could also be used. Furthermore, a time interval could extend over several half-waves of the heating alternating current. It is however advantageous when the time intervals are each an integral multiple of the duration of the half-wave of the alternating current.

In the next step S5, a set value $S_{soll,i}$ is kept constant at the device 7 for controlling the power supply means 6 during time interval $\delta t_i$, and the system is heated at a heating power which is constant for the duration of time interval $\delta t_i$.

In the next step S6 of the temperature control, the voltage which is actually applied to heating device 2 is measured with the aid of the voltage measuring means 4.

The voltage which is actually applied to the heating device 2 is permanently measured during the whole temperature control method when time intervals of the length of a half-wave of the alternating current are used, with an effective voltage value being respectively determined for the heating alternating voltage which is applied.

In another advantageous embodiment the effective current flowing through the heating device is measured with the aid of the current measuring means 5 in addition to the effective voltage actually applied to the heating device. In this case a heating power which is actually employed at the heating device within time interval $\delta t_i$ is determined by multiplying the effective values measured for the current and the voltage.

In the subsequent step S7 of the temperature control, the measured voltage value which is actually present at the heating device is converted into a set value $S_{ist,i}$ according to the calibration curve of FIG. 7.

In the next step S8, the value $S_{soll,i}$ and value $S_{ist,i}$ are compared. When the two values differ from one another by more than a predetermined tolerance value, the set value $S_{soll,i+1}$ is increased for the subsequent time interval by the difference $S_{soll,i}-S_{ist,i}$. Therefore, when the measured heating voltage at the heating device is lower than the voltage first calculated in accordance with the corresponding set value $S_{soll,i}$, the heating voltage converted into a set value $S_{soll,i+1}$ is increased by the amount of the deviation in the subsequent time interval $\delta t_{i+1}$. When the measured heating voltage is higher than the calculated heating voltage $U_{digit,i}$ to be applied, the heating voltage to be applied is lowered by the amount of the deviation expressed in set values in the subsequent time interval $\delta t_{i+1}$. After the new set value $S_{soll,i+1}$ has been calculated, the method goes back again to step S4.

By contrast, when $S_{ist,i}$ and $S_{soll,i}$ differ by less than the predetermined tolerance value from one another, the process is continued for carrying out the time interval incrementation from $\delta t_i$ to $\delta t_{i+1}$ in step S4 again. The previously determined set value $S_{soll,i+1}$ is now adopted in unchanged form.

Instead of the comparison of the set values for the originally calculated heating voltage and the measured heating voltage interpreted as a set value, a direct comparison of the heating voltages or a comparison of the calculated heating power with the measured heating power could also be made. In addition to the above described control method for the heating voltage and the heating power, respectively, by comparing the respectively set values for the calculated and actually measured values, a temperature measurement could also be performed by means of the heat radiation-sensitive photodiode 3 for readjusting the temperature prevailing on the atomizer tube in a similar control operation. Instead of the correction of the set values, the heating power to be applied to the heating device is newly calculated according to the measured temperature and converted into a set value in such an embodiment of the method after each time interval. The newly calculated set value for the corresponding subsequent time interval has possibly to be modified in addition in accordance with the above-described method by the difference between the set values for the calculated heating voltage to be applied within the present time interval and the measured heating voltage.

Figure 3:
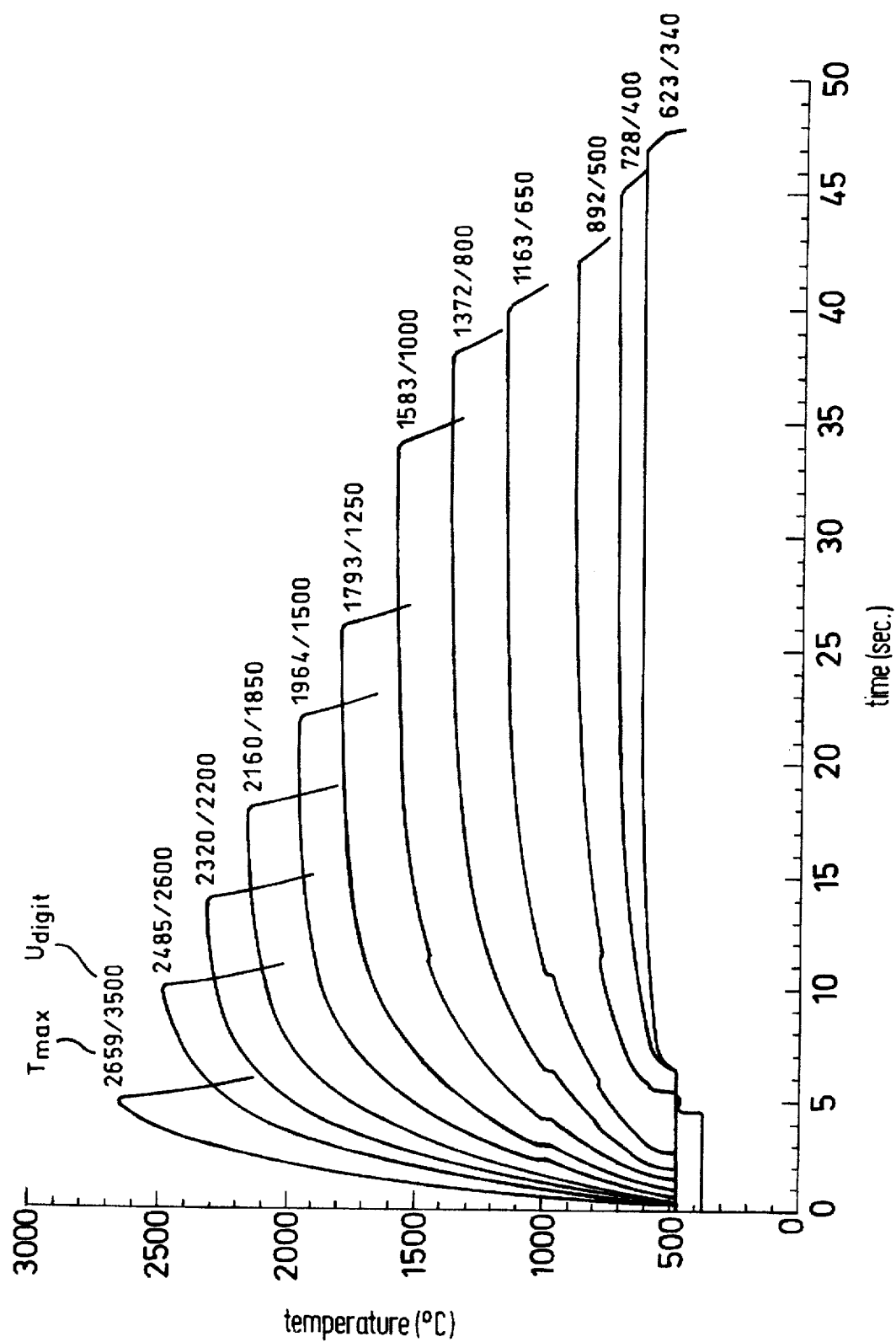
FIG. 3 shows a temperature-time characteristic of a transversely heated tube with the heating power as parameter, which characteristic is used for determining system values in the equilibrium state of the system.
Figure 4:
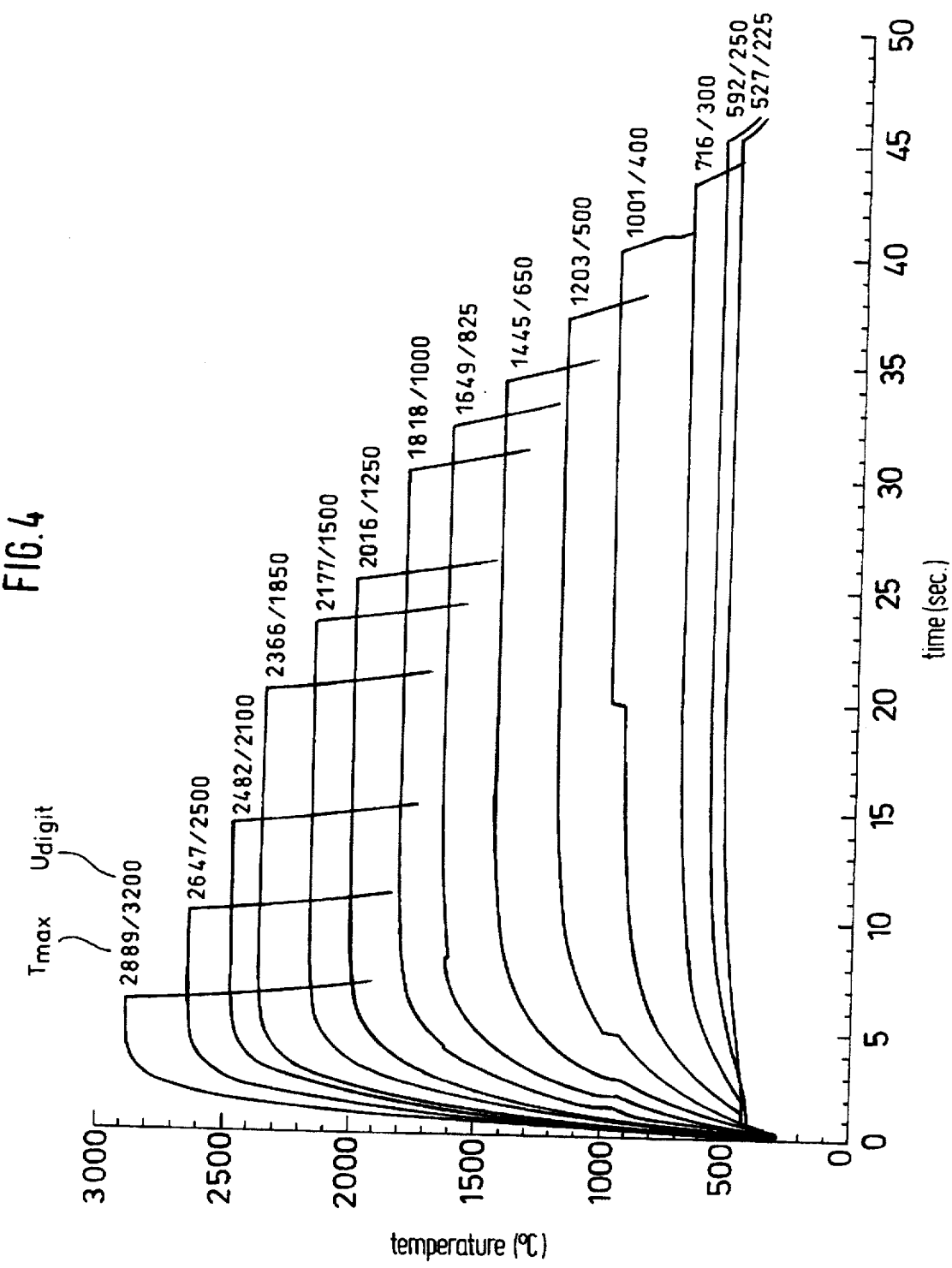
FIG. 4 shows a characteristic according to FIG. 3 but for a longitudinally heated tube.
Figure 5:
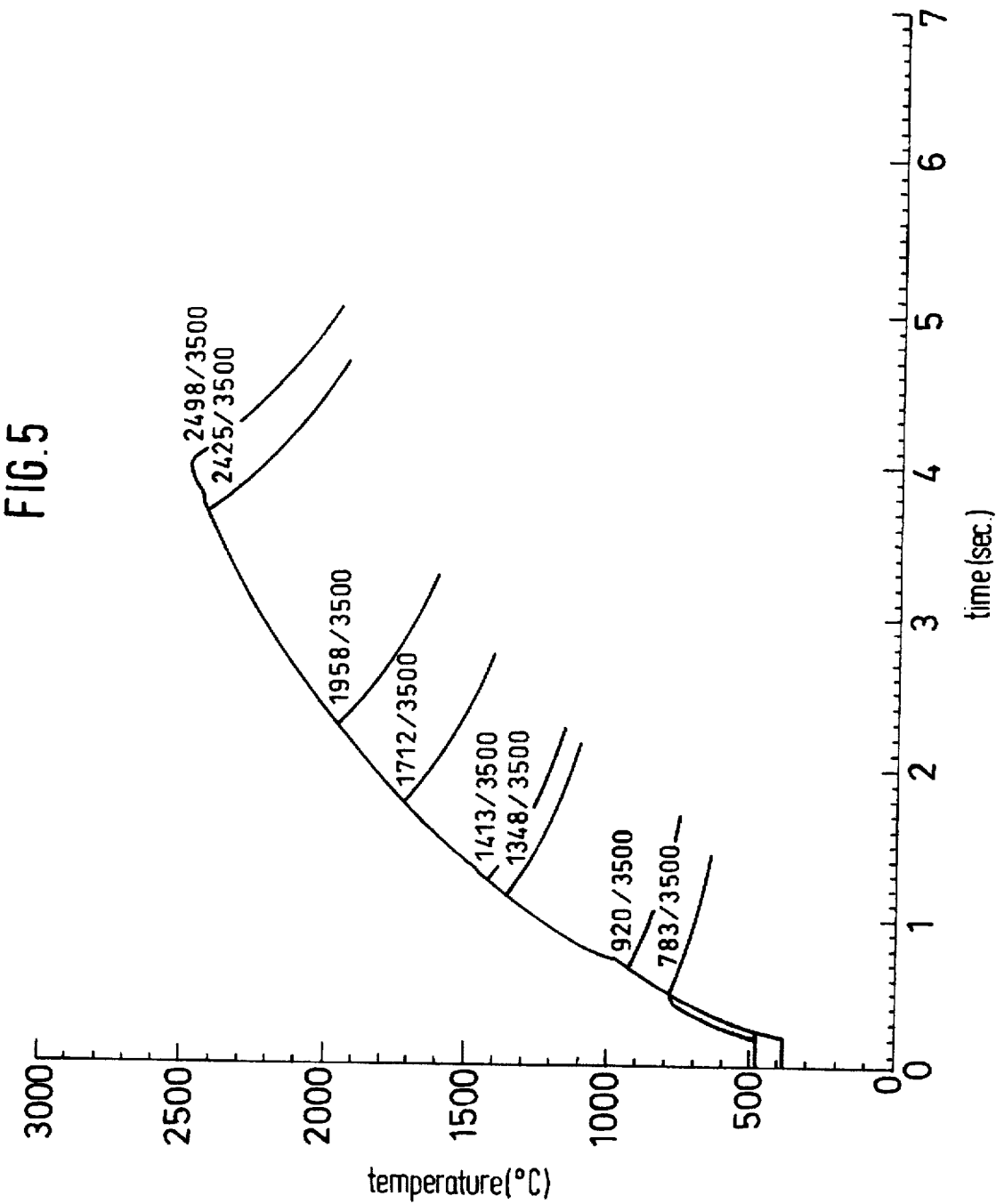
FIG. 5 shows a temperature-time characteristic for the transversely heated tube with the switch-off temperature as parameter, which characteristic is used for determining the system values at maximum heating power.

The empirical determination of the values which are typical of the system and depend on the temperature and temperature curve steepness and regard the dynamic heat capacity $C_w$ and the dissipated power $N_v$ from the heating-up and cooling properties upon the application of different heating powers shall now be discussed in more detail. FIGS. 3 and 5 illustrate temperature-time characteristics with the heating power as parameter for the transversely heated atomizer tube and the longitudinally heated atomizer tube, respectively, for a specific system, i.e. a specific arrangement of an atomizer tube and a heating device. Each of the curves of the characteristics is provided with a pair of values which firstly indicate the maximum temperature achieved and secondly the heating power applied, expressed in values of the effective voltage $U_{digit}$. The temperature of the atomizer tube is measured with the heat-radiation sensitive (calibrated) photodiode 3 for determining said characteristics. The individual curves of the characteristics are recorded over a sufficiently long period to permit the adjustment of an equilibrium state of the atomizer tube in which the steepness of the temperature curves approaches zero and the supplied heating power is thus equal to the outgoing dissipated power. When the heating power is switched off as soon as the equilibrium state has been reached, the atomizer tube is cooled down again, with the cooling rate being the higher the higher the temperature prevailing on the atomizer tube. The values for the dissipated power $N_v$ (T,O) for different temperatures according to the given maximum temperatures of each characteristic curve with the temperature curve steepness T'=0 are directly obtained through the value of the applied heating power N (in accordance with equation (1)) from the characteristics, as are, for instance, illustrated in FIGS. 3 and 4. The corresponding dynamic heat capacity $C_w$ (T,O) is determined by studying the limit value at the time at which the heating power is switched off in each characteristic curve. Since the dynamic heat capacity which is here used, as well as the dissipated power represent each a steady function, the values of the dynamic heat capacity $C_w$ (T,O) and $C_w$ (T, –T') and the dissipated powers $N_v$ (T, O) and $N_v$ (T, –T') are each the same at the moment when the heating power is switched off, with –T' being the limit value of the temperature curve steepness directly after the heating power has been switched off. Therefore, the value for the dynamic heat capacity $C_w$ (T, O) at limit value –T' can directly be calculated after the heating power has been switched off by inserting the value which can directly be determined for the dissipated power $N_v$ (T, O) into equation (1). Since the heating power is zero, the dynamic heat capacity $C_w$ (T, O) becomes $N_v$ (T, O)/T' The value of T' is determined from the characteristics. A parabolic approximation is advantageously performed for obtaining the value of T' in a manner which is exact as possible directly after the heating power has been switched off. However, other approximation methods could also be performed to obtain the value of T' from the measured values according to the characteristic.

Figure 6:
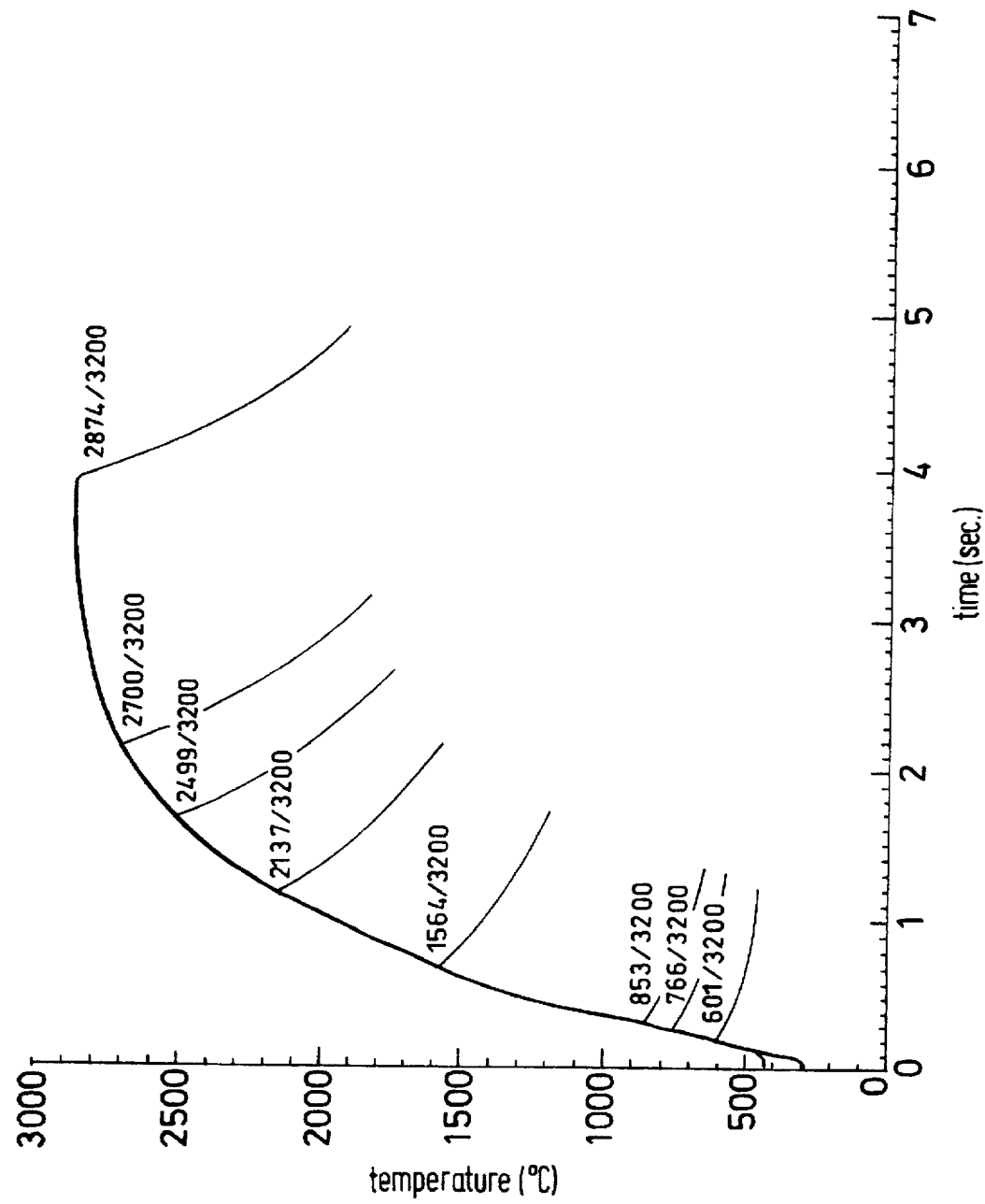
FIG. 6 shows a characteristic according to FIG. 5 but for a longitudinally heated tube.

Furthermore, the dynamic heat capacity and the dissipated power for different temperatures and different temperature curve steepnesses in the non-equilibrium state can be determined in accordance with the present method. To this end, the temperature-time characteristics are determined at a maximum heating power of the heating device. FIGS. 5 and 6 illustrate such characteristics for a transversely heated atomizer tube and a longitudinally heated atomizer tube, respectively. The heating device is operated at maximum heating power and the temperature of the atomizer tube is again measured with photodiode 3. However, the heating power is already switched off after relatively short periods before the thermal system reaches an equilibrium state. A pair of values that firstly indicate the maximum temperature reached and secondly the maximum heating power applied is illustrated in the characteristics of FIGS. 5 and 6, each near a maximum value of each characteristic. By analogy with the cases described above with the system being in the equilibrium state, the dynamic heat capacity $C_w$ (T, T') and the dissipated power $N_v$ (T, T') are now calculated for different temperatures and different steepnesses of temperature curves in accordance with the curves shown is FIGS. 5 and 6 by studying the limit values for the curves directly before and after the switching off of the heating power. Equation (1) is again used for this purpose, with two statements being made for equation (1). Firstly, the limit value of the temperature curve steepness immediately before the switching off of the heating power (i.e., during the heating-up phase) and the maximum heating power are inserted into equation (1); secondly, the limit value of the temperature curve steepness is used immediately after the heating power has been switched off (i.e. in the cooling phase), and the value 0 is inserted for the heating power. On the basis of the above-mentioned condition for the continuity of the functions depending on the temperature curve steepness for the dynamic heat capacity and the dissipated power, one therefore obtains an equation system from two equations with two unknowns on the basis of which the values of $C_w$ (T, T') and $N_v$ (T, T') can unambiguously be determined:.

$$C_w(T, T_1) \times T_1 + N_v(T, T_1) = N \quad (2)$$
$$C_w(T, T1) \times T_2 + N_v(T, T_1) = O$$

In equation (2) $T_1$ and $T_2$ stand for the limit value for the temperature curve steepness before and after the switching off of the heat power. Values for the dynamic heat capacity $C_w$ (T, T') and the dissipated power $N_v$ (T, T') for different temperatures and different temperature curve steepnesses are determined in this way at a heating power maximally applied to the heating device.

The values determined in an equilibrium state and in a non-equilibrium state of the system are each stored in tables of values for the dynamic heat capacity $C_w$ and the dissipated power $N_v$ for specific values of temperature T and temperature curve steepness T'. The values of $C_w$ and $N_v$ are determined by linear interpolation for such desired temperature values and temperature curve steepness values that do not correspond with a pair of values of (T, T') stored in the table. In practice, it has been found to be enough when the dynamic heat capacity and the dissipated power are determined with a multitude of heating powers in the equilibrium state and with a maximum heating power in the non-equilibrium state with a multitude of temperatures and when the values of $C_w$ and $N_v$ are calculated for intermediary values of the temperature curve steepness and the desired temperature by interpolation. This considerably reduces the time needed for preparing the tables of values according to the respective temperature-time characteristics with successive heating-up processes. On the other hand, the method could be modified such that the determination of the dynamic heat capacity $C_w$ and the dissipated power $N_v$ in the non-equilibrium state is determined at a multitude of heating powers according to formula ((2) instead of the sole use of the maximally available heating power.

Figure 8:
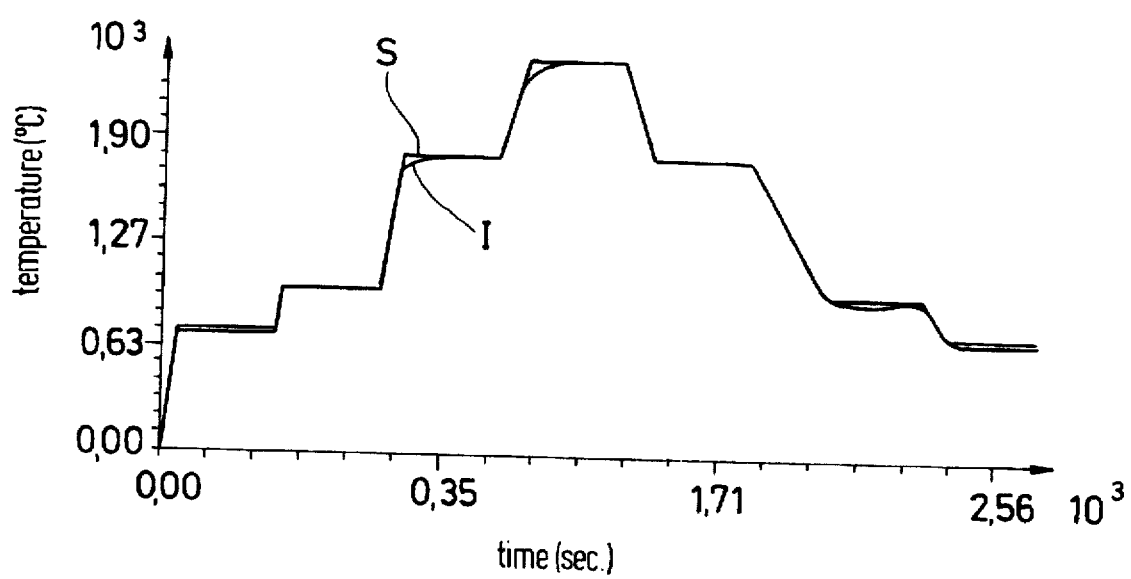
FIG. 8 is a graphic representation of the temperature-time characteristic of a system for a desired behavior and a characteristic actually achieved with the method of the invention for a longitudinally heated tube.

FIG. 8 illustrates an example of a complicated desired temperature curve S and of the corresponding temperature curve I actually realized with the inventive method for a longitudinally heated tube. As becomes apparent from the illustration, the predetermined desired temperature curve can be obtained with high accuracy.

We claim:

1. A method for controlling the temperature of a system comprising the steps of:

empirically determining the dynamic heating and cooling characteristics of the system;

dividing a desired temperature curve for the system to follow into predetermined time intervals;

assigning a desired temperature to each time interval;

applying an initial heating power based on the empirically determined dynamic heating and cooling characteristics to a heating device during each time interval;

measuring the actual heating power applied to said heating device during said predetermined time interval, and when the actual heating power deviates from the initial heating power by more than a predetermined tolerance value within the predetermined time interval, changing the heating power for a following predetermined time interval in response to said deviation.

2. The method of claim 1, where the empirically determined heating and cooling characteristics include dynamic heat capacity, dissipated power and temperature slope.

3. The method of claim 2, wherein the values for the dynamic heat capacity and the dissipated power are calculated according to the following two formulae:

$$C_w(T,T_1) \times T_1 + N_v(T, T_1) = N$$

$$C_w(T, T_1) \times T_2 + N_v(T, T_1) = 0$$

wherein $T'_1$ and $T'_2$ represent temperature curve slope values determined immediately before and after switching off of the heating power, and $C_w(T, T'_1)$ and $N_v(T, T'_1)$ are the values which depend on temperature T and temperature slope $T'_1$ during the heating-up period directly before switching off and N is the constant heating power applied before switching off.

4. The method of claim 3, wherein the heating power to be applied within a predetermined time interval is calculated according to the formula $$N_i = C_w(T_i, T_i) \times T'_i + N_v(T_i, T_i)$$

wherein $N_i$ is the heating power supplied to the system in the i-th time interval, $T_i$ is the desired temperature of the i-th time interval, $T'_i$ is a temperature slope corresponding to the desired heating-up rate in the i-th time interval, which slope is determined by a difference of the desired temperatures of the i-th and the i-1st time intervals divided by the length of the i-th time interval, and $C_w$ and $N_v$ are the dynamic heat capacity and the dissipated power, respectively.

5. The method of claim 3, wherein the temperature slope is determined by heating the system using a predetermined heating power to a specific temperature at which the heating power is switched off, and the temperature slope is measured directly before and directly after the heating power is switched off.

6. The method of claim 3 wherein a table of values for the dynamic heat capacity $C_w$, dissipated power $N_v$, and temperature slope are determined for a multitude of desired temperature values.

7. The method of claim 6, wherein the dynamic heat capacity and the dissipated power are determined at a multitude of values for the heating power in an equilibrium state of the system, in which the dissipated power is equal to the heating power, and when maximum heating power is supplied to the system at a multitude of temperature values in a non-equilibrium state.

8. The method of claim 7, further comprising the steps of:
changing a component of the system; and
generating a table of values for the system, with the changed component.

9. The method of claim 1, wherein the heating power to be applied within a time interval is determined in accordance with the desired temperature and the temperature curve slope within the respective interval from a temperature-time characteristic empirically determined with a plurality of different heating powers.

10. The method of claim 9, further comprising the step of forming a table of values for the heating power for a respective multitude of temperatures and temperature curve slopes.

11. The method of claim 10, wherein the table of values is stored in a storage medium.

12. The method of claim 10, further comprising using linear interpolation for determining the heating power at values other than those contained in the table of values for the desired temperature and the temperature curve slope.

13. The method of claim 1, wherein the actual heating power applied to the heating device is determined by measuring the voltage applied to said heating device and converting said value into a heating power.

14. The method of claim 1, further comprising the steps of:
measuring an instantaneous temperature of the system within each time interval;
comparing said instantaneous temperature with the desired temperature; and
when a deviation of said instantaneous temperature from the desired temperature exceeds a predetermined value, changing the desired temperature of a successive time interval in response to said deviation.

15. The method according to claim 1, wherein the temperature curve is divided into equal time intervals.

16. The method of claim 1, wherein an alternating current is used in said heating device for heating said system.

17. The method of claim 16 wherein said time-interval extends over a half cycle of the alternating current.

18. The method of claim 1, wherein phase angle control is used in said heating device.

19. The method of claim 1 wherein the system is an atomic spectroscopy furnace.

20. In a system having a heater and power control means for applying power to the heater to control the temperature of the system, a method for controlling temperature in accordance with a desired temperature curve defined over predetermined time intervals, the method comprising the steps of:
determining empirically dynamic heating and cooling characteristics of the system to define a calibration curve;
causing said power control means to apply power to said heater to cause said system to follow said desired temperature curve in accordance with a temperature and a curve slope defined by said desired temperature curve by using said calibration curve to define a calibration set value for said power control means;
determining actual power supplied to said heater by said power control means during each time interval;
converting the actual power determined into a comparative set value for said power control means using said calibration curve;
comparing said comparative set value to said calibration set value to determine if said comparative set value differs from said calibration set value by more than a predetermined difference; and
changing the calibration set value of a following time interval when said comparative set value differs from said calibration set value by more than said predetermined difference.

21. The method of claim 20, wherein when the deviation of the set value from the set comparative value is exceeded by a predetermined tolerance value within a time interval, the set calibration value of successive time interval is changed by adding an amount equal to a difference between the set value and the set comparative value.

22. The method of claim 21, wherein the set values correspond to operating angles of phase angle control of said power.

* * * * *